United States Patent [19]

Daly

[11] Patent Number: 4,571,985
[45] Date of Patent: Feb. 25, 1986

[54] METHOD AND APPARATUS FOR MEASURING THE HYDRAULIC CONDUCTIVITY OF POROUS MATERIALS

[75] Inventor: Charles J. Daly, Denver, Colo.

[73] Assignee: The United States Army Corps of Engineers as represented by the Secretary of the Army, Washington, D.C.

[21] Appl. No.: 552,883

[22] Filed: Nov. 17, 1983

[51] Int. Cl.⁴ ............................................. G01N 15/08
[52] U.S. Cl. .............................................. 73/38; 73/37
[58] Field of Search ......................... 73/38, 863.21, 37

[56] References Cited

U.S. PATENT DOCUMENTS

| | | | |
|---|---|---|---|
| 2,268,627 | 1/1942 | Silverman | 73/38 |
| 2,778,243 | 1/1957 | Darrieus | 74/573 R |
| 3,289,467 | 12/1966 | Parker et al. | 73/61.4 |
| 3,336,793 | 8/1967 | Tuttle | 73/38 |
| 3,380,292 | 4/1968 | Le Fournier | 73/38 |
| 3,435,663 | 4/1969 | Lamballerie | 73/38 |
| 3,683,674 | 8/1972 | Roy | 73/38 |
| 3,696,688 | 10/1972 | Goodrich et al. | 74/573 |
| 4,200,003 | 4/1980 | Miller | 74/574 |

FOREIGN PATENT DOCUMENTS 787951 12/1980 U.S.S.R. ................................. 73/38

Primary Examiner—Stewart J. Levy
Assistant Examiner—Hezron E. Williams
Attorney, Agent, or Firm—Darrell E. Hollis

[57] ABSTRACT

A method and apparatus for directly measuring the hydraulic conductivity of porous materials at various degrees of saturation, the invention involves determination of the rate of rotation under dynamic equilibrium of concentric cylinders having a partially saturated porous material disposed in an annular space between the concentric cylinders, the rate of rotation being directly related to the hydraulic conductivity of the material. The hydraulic conductivity of the material can thus be determined without the need for measuring fluid discharge and piezometric head gradient as is necessary in prior art determination of hydraulic conductivity.

20 Claims, 3 Drawing Figures

METHOD AND APPARATUS FOR MEASURING THE HYDRAULIC CONDUCTIVITY OF POROUS MATERIALS

STATEMENT OF GOVERNMENT INTEREST

The invention described and claimed herein may be manufactured and used by or for the Government of the United States of America for governmental purposes without the payment of royalties thereon or therefor.

BACKGROUND OF THE INVENTION

1. Field of the Invention

The invention relates generally to measurement of the hydraulic conductivity of porous materials and particularly to a method and apparatus for directly measuring hydraulic conductivity of porous materials at various degrees of saturation without the need for measuring fluid discharge and piezometric head gradient.

2. Background of the Invention

Existing methodology and apparatus for measuring the hydraulic conductivity of porous materials exhibit characteristics which limit the accuracy of hydraulic conductivity measurements thereby produced. Prior apparatus, generally known as permeameters, are typically configured such that dissolved gases which are contained in fluids supplied to a sample often come out of solution and affect flow within the sample. Similar errors can be introduced in prior permeameters by temperature variations which affect viscosity, these thermal variations being difficult to control with prior apparatus. Further, small discharges and gradients are difficult to measure and, in prior apparatus, must be measured in order to produce usable results. Errors are also introduced in prior apparatus by factors as simple as evaporation losses from the reservoirs which supply fluid to the samples.

As will be discussed in more detail hereinafter, and immediately prior to a detailed description of the preferred embodiments of the invention, present methods for measuring hydraulic conductivity of unsaturated and saturated materials depend on the measurement of fluid discharges and piezometric head gradients. In these prior procedures, a fluid is typically allowed to pass through a sample of material on the way from a first reservoir to a second reservoir. Examples of such prior art permeameters include the constant head permeameter and the variable head permeameter which are well known in the art. For unsaturated materials, a permeameter must be operated at air pressures less than the air entry pressure of the porous plate materials forming the interfaces between the sample and the fluid reservoirs.

Prior permeameters and similar apparatus disclosed in issued United States patents include U.S. Pat. No. 3,435,663 to De Lamballerie which discloses apparatus for determining the permeability of a ground sample which is placed in a chamber with drilling mud with heat and pressure being applied to the sample to force the mud through the sample. Particular attention is given in the apparatus of De Lamballerie for compensating for temperature conditions and differential pressure conditions.

U.S. Pat. No. 3,683,674 to Roy discloses a porosimeter for measuring the size-volume distribution of porosity of a porous member. The apparatus of Roy includes a rotating sample chamber. However, the device of Roy is not capable of making the same measurements as that of the present permeameter and Roy does not disclose the particular apparatus of the present invention.

Russian Pat. No. 787,951 also describes a porosity tester which utilizes a rotating drum. However, in a manner similar to that described above relative to Roy, the Russian patent does not disclose apparatus capable of performing the permeability or hydraulic conductivity measurements to which the present invention is addressed.

Accordingly, the present invention allows the measurement of hydraulic conductivity without the inaccuracies and measurement problems associated with the prior art. By measurement of hydraulic conductivity from the motion of fluid which is fully contained within a porous sample, the present invention eliminates measurement difficulties associated with both dissolved gases and evaporation and also minimizes thermal affects by allowing better temperature control within the test system. Since it is not necessary to measure discharge or piezometric head gradients in the practice of the present invention, errors inherent in such measurements with existing technology are obviated, the present invention requiring only measurements which can be made in a precise manner. Further, under unsaturated conditions, measurement problems inherent in the prior art and which are associated with the use of porous plates and the like are eliminated. The present invention thus exhibits substantial advantages over the prior art.

SUMMARY OF THE INVENTION

The present invention provides a method and apparatus for directly measuring the hydraulic conductivity of porous materials whether or not fully saturated. The invention particularly allows the determination of hydraulic conductivity through measurement of parameters which can be precisely determined, such as apparatus geometry, total fluid content within the apparatus, and the magnitude of and rate of fall of a mass associated with the apparatus. The invention particularly obviates the need to measure either discharge or piezometric head gradients in a direct manner, thereby eliminating errors inherent in the measurement of these difficult-to-measure parameters.

The apparatus of the invention substantially comprises two concentric cylinders having an annular space therebetween, the annular space holding a porous material sample. The concentric cylinders are mounted to rotate as a unit about a central axis with a hanging mass being moutable from the axis of rotation to provide a selected torque to the rotating cylinder pair. The annular space between the concentric cylinders is uniformly filled with a dry porous sample material. The cylinder pair is then precisely balanced with no external torque being applied. The balancing may require the placing of balancing weights about the surface of the cylinder pair. The sample is then wetted to a desired degree of saturation prior to initiation of actual testing.

In operation, the free liquid, typically water, within the sample material is free to move through the sample material as the cylinder pair and enclosed sample rotate about the central axis of the cylinder pair. In time, the cylinder pair and enclosed sample held stationary, an equilibrium is established wherein the greater part of the free liquid settles, under the influence of gravity, to the lower portion of the annular space between the concentric cylinders. Releasing the cylinder pair, a torque then applied to the cylinder pair raises the wet portion of the annular space to a point where an equal and opposite torque to the applied torque is generated. Since the liquid is free to move within the annular space, the liquid will then move in the direction of lower head, that is, the liquid will try to re-establish equilibrium. In order for the applied torque to be continually balanced by the torque which is generated, the movement of the liquid must be compensated for by rotation of the cylinder pair. Accordingly, the cylinder pair rotation becomes steady as a new dynamic equilibrium is established. This rate of rotation of the cylinder pair, determined by the steady rate of all of the hanging mass under the dynamic equilibrium, is directly related to the hydraulic conductivity of the sample material. Hydraulic conductivity can thus be calculated under both saturated and unsaturated conditions.

Accordingly, it is an object of the present invention to provide a method and apparatus for directly measuring the hydraulic conductivity of porous materials at various degrees of saturation without direct measurement of either discharge or piezometric head gradient, the measurements upon which the present methodology depends being subject to precise measurement.

It is another object of the present invention to provide apparatus for measuring hydraulic conductivity of a sample material, the apparatus comprising concentric cylinders having an annular space disposed therebetween within which a sample material is placed with partial saturation of the material, the rate of rotation of the concentric cylinders under dynamic equilibrium being measured and being directly related to the hydraulic conductivity of the sample.

It is a further object of the present invention to provide a method for measuring the hydraulic conductivity of a porous material without the need for measuring discharge piezometric head gradient.

Further objects and advantages of the present invention will become more readily apparent in light of the following detailed description of the preferred embodiments.

DESCRIPTION OF THE PREFERRED EMBODIMENTS

Figure 1:
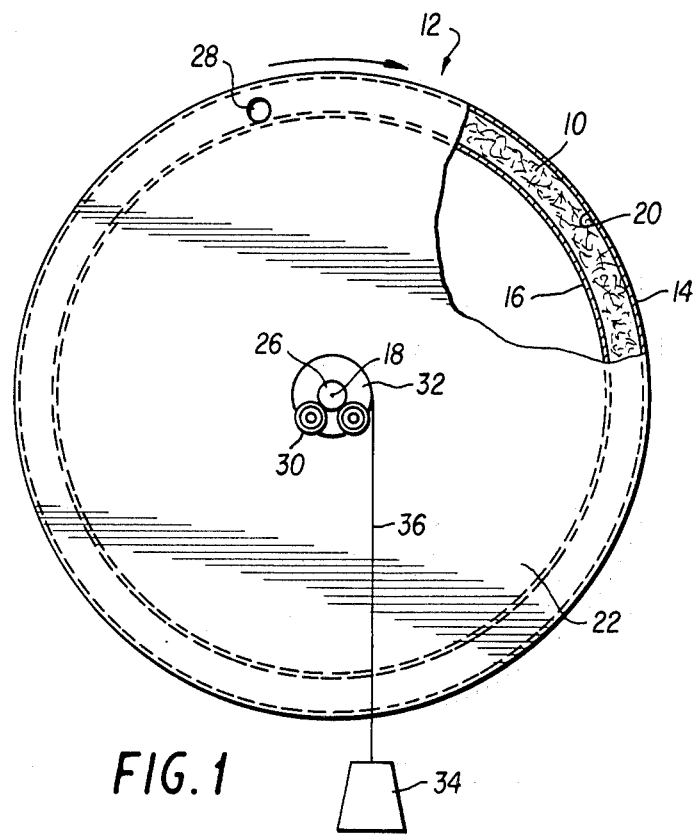
FIG. 1 is an idealized end view of the present apparatus which is partially cut away.
Figure 3:
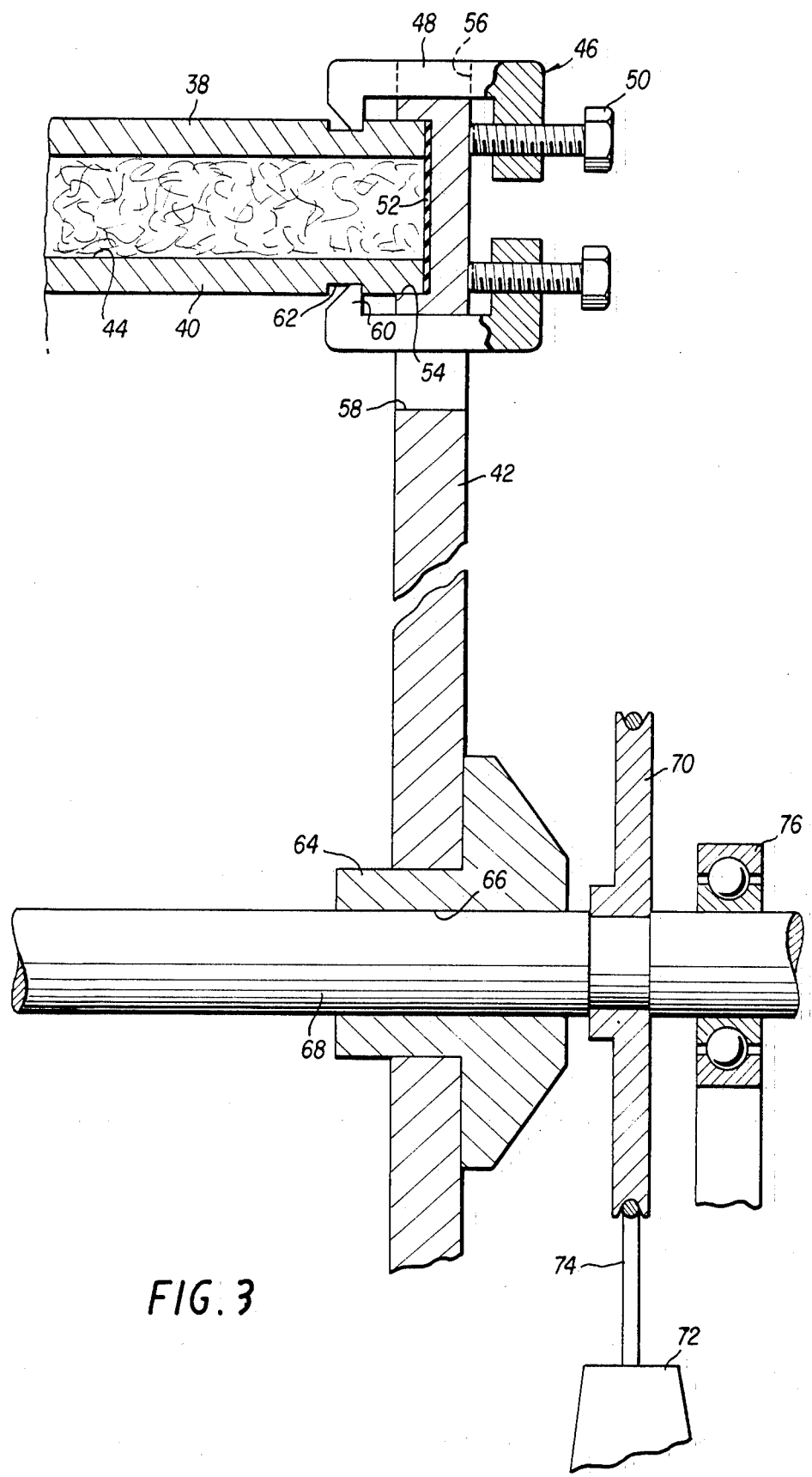
FIG. 3 is a detailed view in partial section of an arrangement for mounting the cylinders to a rotary shaft and for mounting end covers to the cylinders.

In order to fully appreciate the disclosure particular to the present invention, certain technical background information is hereinafter related. In particular, a porous material such as is represented at 10 in FIGS. 1 and 3 is characterized by a network of a large number of minute, interconnected pores. At full saturation, all such pores contain fluid. At varying degrees of partial saturation, only those pores smaller than a certain size are filled. As is known in the art of fluid mechanics, fluid flow results from the establishment of differences of potential energy between points within a fluid continuum. In the case of flow through porous materials, fluid potential energy is generally expressed in terms of piezometric head h, which is a function of fluid specific weight $\gamma$, pressure p, and elevation z, this relationship being expressed as follows:

$$h = p/\gamma + z$$

For isotropic materials, flow at every point is in a direction opposite to the local gradient of h (represented by $\nabla h$), while the rate of flow depends upon the magnitude of $\nabla h$.

When considering an arbitrary cross sectional area A cutting through a porous material in a direction perpendicular to $\nabla h$, viscous resistance acts within the fluid and along the walls of the pore channel network to effectively control the discharge of fluid through area A. For a certain range of piezometric head gradients, discharge Q is directly proportional to $\nabla h$. The constant of proportionality for saturated flow is the hydraulic conductivity K; the relationship being expressed as follows:

$$Q/A = -K\nabla h$$

In the case of unsaturated porous materials, only a portion of the total pore channel network contributes to flow. The discharge-gradient relationship must then account for the fact that unsaturated hydraulic conductivity is a function of the degree of saturation, expressed as the volume of fluid per unit volume of porous material $\theta$, or as represented by the following expression:

$$Q/A = -K(\theta)\nabla h$$

As has been noted above, existing methods for estimating K for saturated materials depend upon simultaneous measurement of discharge and piezometric head gradient. Such methodology involves the use of devices such as the constant head permeameter and the falling head permeameter, these devices holding a uniform sample in a chamber of known cross-sectional area and length. In these prior devices, a supply reservoir and a receiving reservoir are connected to opposite ends of the sample chamber. Piezometric head in the reservoirs, and thus $\nabla h$ through the sample are determined. The discharge through the sample can be collected and measured.

For unsaturated materials, $K(\theta)$ can be determined by modifying the constant head permeameter or the falling head permeameter. Samples held within the chamber are typically bounded at either end by a porous ceramic, or fritted glass plate. When wetted, the plates will pass fluid, but not air, as long as the air pressure within the sample is less than an established maximum known as the air entry pressure of the plates. The desired degree of saturation of the sample is obtained by applying a specific air pressure directly to the sample held between the plates. The introduction of air into the sample chamber displaces part of the fluid from the sample. Fluid exists the sample chamber via the plates leaving the sample at the desired degree of saturation. Applied air pressure is necessarily limited by the rated air entry pressure of the porous plates holding the sample. Accordingly, for a given set of plates, K can be determined only over a limited range of saturation. For determination involving unsaturated materials, the prior devices must therefore be operated at air pressures less than the air entry pressure of the plate materials forming the interfaces between the sample and the fluid reservoirs. Among other advantages, the present apparatus is not subject to the limitations on attainable degrees of saturation due to plate components when measuring the hydraulic conductivity of unsaturated materials.

Figure 2:
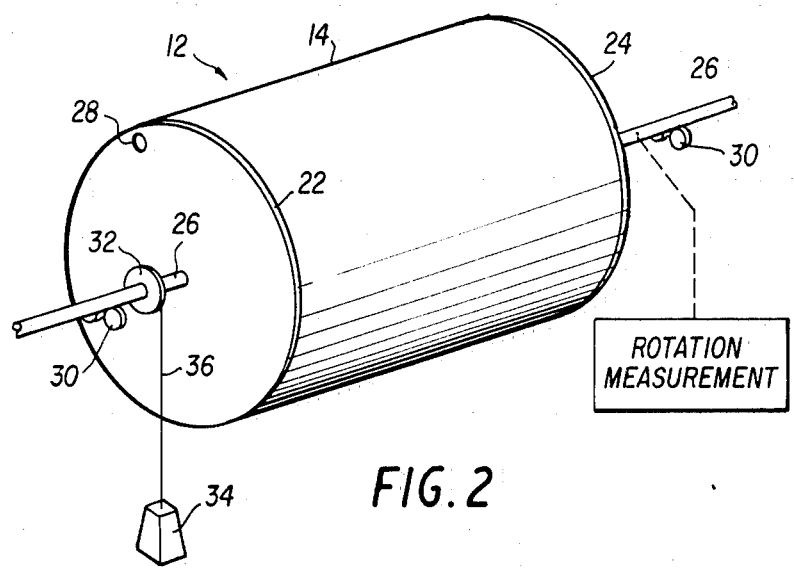
FIG. 2 is an idealized perspective view of the present apparatus.

Given this background, reference is particularly made to FIGS. 1, 2 and 3 wherein a permeameter 12 according to the present invention is seen to be comprised of outer and inner right circular cylinders 14 and 16, these cylinders 14 and 16 being concentric about a central axis of rotation 18. The concentric cylinders 14 and 16 are of equal length and define an annular chamber 20 between the inner surface of the outer cylinder 14 and the outer surface of the inner cylinder 16. The annular chamber 20 is seen to constitute a narrow annulus of uniform thickness and receives the porous material 10 therein. Cover plates 22 and 24 mount to the ends of the cylinders 14 and 16 and seal the annular chamber 20 at each end. The cover plates 22 and 24 act to hold the cylinders 14 and 16 in place and to provide a structural connection of the cylinders about the central axis 18 such as by mounting of a central rod 26. The central rod 26 can be rotated in any known manner but particularly mounts the cylinder assembly so that the cylinder assembly can rotate freely about the axis of rotation 18. The cover plates 22 and 24 can be removed for filling of the annular chamber 20 with the porous material 10 which is to be tested. Ports 28 (not shown on the cover plate 24) can be provided in each of the cover plates for permitting the release or injection of air or fluid into the annular chamber 20.

The central rod 26 preferably traverses the length of the cylinders in a "concentric" manner along the axis of rotation 18 and extends beyond each of the cover plates 22 and 24. The central rod 26 is secured to the cover plate in one of any number of known arrangements. The rod 26 is supported by bearings such as the bearings represented at 30 to allow the cylinder assembly to turn freely about the central axis 18. A pulley-like collar 32 is fixedly mounted to the central rod 26 at one end of the rod, the collar 32 mounting a weight 34 which hangs from said collar by means of a line 36. The hanging weight 34 provides a selected torque to the permeameter 12. Selection of collar diameter allows for selection of particular moment arms. The line 36 can take the form of a fine thread or wire attached to the hanging mass and wound about the collar 32. It is to be understood that the weight 34 can be hung directly from the rod 26 itself.

Operation of the present permeameter 12 includes the loading of the dry porous material 10 into the annular chamber 20. Care must exercised to maintain approximate uniformity of the porous material 10 within the annular chamber 20. The cover plates 22 and 24 are then assembled onto the outer and inner cylinders 14 and 16 and the cylinder assembly is then mounted in a horizontal orientation on the bearings 30. It is to be understood that the weight 34 is not mounted to the rod 26 at this point. The ports 28 are then sealed and the permeameter 12 is allowed to turn freely about the axis of rotation 18. Balancing weights (not shown) can then be secured to the permeameter 12 until no tendency to rotate to any preferred orientation is noted. In other words, the assembly is then "balanced". The porous material 10 is then "wetted" to the desired degree through the ports 28 and the assembly is prepared for testing by allowing settlement of part of the fluid to the lower portion of the annular chamber 20.

A selected mass constituting the weight 34 is then hung from the collar 32 with the immediate result being the tipping of the "wet" portion of the annular chamber 20 so as to create a torque, caused by fluid mass, which balances the torque due to the hanging weight 34. Since the fluid in the porous material is free to move, it will move in the direction of lower piezometric head, that is, returning toward the bottom of the annular chamber 20. As it does so, the torque compensating the hanging mass is automatically maintained by unassisted rotation of the device. As long as the magnitude of the weight 34 is less than a critical maximum value, the system reaches a state of dynamic equilibrium. Under dynamic equilibrium, the steady rate of rotation can be determined by measuring the rate of fall of the weight 34. If the magnitude of the weight 34 exceeds the critical value, the permeameter 12 would accelerate uncontrollably. However, this critical value can be easily estimated and selected such that the mass of the weight 34 does not exceed the critical value.

Referring now to FIG. 3, a particular arrangement for mounting the cover plates to the cylinders is shown. In the embodiment of FIG. 3, outer and inner cylinders 14 and 16 are mounted to cover plate 22 as seen at one end of the apparatus. In a similar fashion, a second cover plate 24 is mounted to the other end of the cylinders 14 and 16.

Clamps 46 comprised of L-shaped body members 48 and screws 50 clamp the cover plate 22 to the ends of the cylinders 14 and 16 as shown. A gasket 52 can be provided in the bottom of receiving recess 54 formed in the interior face of the cover plate 22 so that the annulus 20 is sealed. Portions of the body members 48 extend through slots 56 and 58 formed in the cover plate 22 so that toe portions 60 of the clamps 46 can engage and bear against recesses 62 formed in surface portions of the cylinders 14 and 16, thereby allowing the screws 50 to be rotated and to tighten the cover plate 22 to the ends of the cylinders 14 and 16.

An annular bushing 64 having a central aperture 66 extending therethrough can conveniently mount central rod 26 centrally of the cover plate 22. Appropriate mounting apertures and screw elements can be employed to mount the bushing 64 to the cover plate and to the central rod 26 in a known manner. A collar 32 mounting a weight 34 by means of a line 36 attaches to the central rod 26 as described above. Further, bearings 30 support the central rod 26 and thus the assembly in a known fashion.

DESCRIPTION OF THE HYDRAULIC CONDUCTIVITY CALCULATION PROCEDURE

With reference to the described embodiment consider the following notation:

| | | |
|---|---|---|
| C | Specific moisture capacity of the porous material sample | $[L^{-1}]$ |
| h | Piezometric head | $[L]$ |
| K | Hydraulic conductivity | $[LT^{-1}]$ |
| L | Cylinder length | $[L]$ |
| M | Mass of the hanging weight | $[M]$ |
| p | Fluid pressure | $[MT^{-2}L^{-1}]$ |
| | $r_1$ Outer radius of the inner cylinder | $[L]$ |
| | $r_2$ Inner radius of the outer cylinder | $[L]$ |
| $R = (r_1 + r_2)/2$ | Average radius of the annulus | $[L]$ |
| t | Time | $[T]$ |
| V | Volume of water in the annulus | $[L^3]$ |
| z | Elevation of a point on the annulus | $[L]$ |
| $\beta$ | Angular coordinate measured around the annulus; $\beta=0$ or $2\pi$ at the top of the annulus; measured positive in the direction of rotation of the cylinder pair | [radians] |

| | | |
|---|---|---|
| γ | Specific weight of the fluid | $[ML^{-2}T^{-2}]$ |
| θ | Volumetric water content of the porous material | $[L^3 L^{-3}]$ |
| λ | Average piezometric head in the annulus | $[L]$ |
| ξ | Porosity of the porous material | $[1]$ |
| π | 3.14159... | $[1]$ |
| ρ | Density of the fluid | $[ML^{-3}]$ |
| σ | Moment arm of the hanging weight | $[L]$ |
| $\phi = p/\gamma$ | Pressure head | $[L]$ |
| ω | Rate of rotation of the cylinder pair | $[radians\, T^{-1}]$ |

Under conditions of dynamic equilibrium, the rate of mass flow into a sector $(\beta, \beta + \Delta\beta)$ of the annulus equals the rate of mass flow out of that sector. In the analysis of mass balance only the fluid needs to be considered. As the annulus rotates at a steady rate, the rate at which fluid is carried into a sector is:

$$\frac{dm_1}{dt} = \theta \rho \frac{L}{2}(r_2^2 - r_1^2)\omega$$

The rate at which mass flows into (or out of) a sector due to a piezometric head gradient is:

$$\frac{dm_2}{dt} = -\rho L(r_2 - r_1)\frac{K}{R}\frac{dh}{d\beta}$$

Writing a flow balance into and out of a sector yields:

$$\theta\rho\frac{L}{2}(r_2^2 - r_1^2)\omega - \left[\theta\rho\frac{L}{2}(r_2^2 - r_1^2)\omega + \frac{\rho L}{2}(r_2^2 - r_1^2)\omega\frac{d\theta}{d\beta}\Delta\beta\right] +$$

$$\left[-\rho L(r_2 - r_1)\frac{K}{R}\frac{dh}{d\beta}\right] - \left[\rho L(r_2 - r_1)\frac{K}{R}\frac{dh}{d\beta} - \frac{\rho L}{R}(r_2 - r_1)\frac{d}{d\beta}\left(K\frac{dh}{d\beta}\right)\Delta\beta\right] = 0$$

Or, since $R = (r_1 + r_2)/2$:

$$-R^2\omega\frac{d\theta}{d\beta} + \frac{d}{d\beta}\left[K\frac{dh}{d\beta}\right] = 0$$

Integrating over $\beta$:

$$-R^2\omega\theta + K\frac{dh}{d\beta} = \text{constant}$$

Note: $h = \psi + z = \psi + R(1 + \cos\beta)$ $$\frac{dh}{d\beta} = \frac{d\psi}{d\beta} - R\sin\beta.$$

Over the range of saturation in the annulus assume:

$\theta = C\psi + \xi$ and $K =$ constant.

Defining:

$$u = \frac{-R^2\omega C}{K}$$

the governing differential equation for pressure head in the annulus becomes:

$$\frac{d\psi}{d\beta} + u\psi = R\sin\beta + \lambda u,$$

where $\lambda$ is a constant to be determined. The solution to the governing equation must be periodic, i.e., $\psi(\beta=\alpha) = \psi(\beta=\alpha+2\pi)$. Therefore the solution can be written:

$$\psi(\beta) = \frac{a_o}{2\pi} + \frac{1}{\pi}\sum_{n=1}^{\infty}[a_n \cos n\beta + b_n \sin n\beta]$$

A simple procedure yields the coefficients:

$$a_o = 2\pi\lambda$$

$$a_1 = \frac{-R\pi}{u^2 + 1}$$

$$a_n = 0 \; n > 1$$

$$b_1 = \frac{R\pi u}{u^2 + 1}$$

$$b_n = 0 \; n > 1$$

or:

$$\psi(\beta) = \frac{R}{u^2 + 1}[u \sin\beta - \cos\beta] + \lambda$$

Two independent equations are used to determine the unknowns $\lambda$ and $u$; they involve the volume of water in the annulus, and the balance of torque. In the case of the volume of water:

$$\frac{L}{2}(r_2^2 - r_1^2)\int_0^{2\pi}\theta(\beta)d\beta = V$$

from which it is determined that:

$$a_o = \frac{2}{C}\left[\frac{V}{L(r_2^2 - r_1^2)} - \pi\xi\right] = 2\pi\lambda.$$

The equation for the balance of torque:

$$\rho\frac{RL}{2}(r_2^2 - r_1^2)\int_0^{2\pi}\theta(\beta)\sin\beta \, d\beta + M\sigma = 0$$

yields $$b_1 = \frac{-M\sigma}{\rho R^2 LC(r_2 - r_1)} = \frac{R\pi u}{u^2 + 1}$$

Defining:

$\phi = b_1/R\pi$ the last equation becomes:

$\phi u^2 - u + \phi = 0$ from which:

$$u = \frac{1 \pm \sqrt{1-4\phi^2}}{2\phi}.$$

Analysis of the stability of the rotation shows that the minus sign is appropriate in the above equation. Finally:

$$K = \frac{-R^2\omega C}{u}.$$

Consider the following data for a silty porous material:
ξ=0.395
C=0.001/cm.
Suppose the invention is constructed such that:
L=25.4 cm
$r_2$=24.765 cm
$r_1$=22.86 cm
σ=5. cm,
and operated under the following test conditions:
M=100. g
τ=1. g/cm$^3$.
Suppose that the device rotates unassisted at a steady rate of 0.5 radians/day. The above can be used to show that:
$a_o$= −312.125 cm
λ= −49.676 cm
φ= −0.2436
u= −0.2601
K=1.090 cm/day
The value of K may be assumed to be the hydraulic conductivity of the sample at the average pressure head λ, corresponding to the volumetric water content:

$$\theta = C\lambda + \xi = 0.345.$$

Different total volumes of water V would enable the calculation of K at other pressure heads and water contents.

For a given value of K the invention can be shown to have a stable and an unstable mode of operation depending on the applied torque Mσ. This shows that instability in the form of uncontrolled acceleration of the cylinder pair occurs for Mσ greater than a critical value. Instabilities are avoided by selection of appropriate M and/or σ. For K assumed to be 1 cm/day, and all other test parameters as previously noted, the figure shows that the invention operates in a stable mode for torque less than 1025. g−cm. The maximum possible rate of rotation of the cylinder pair under the stated conditions is 1.76 radians/day for Mσ=1025. g−cm.

While the invention has been described relative to particular embodiments, it is to be understood that the scope of the invention is to be defined by the definitions provided by the appended claims.

What is claimed is:

1. Apparatus for measuring a quantity directly related to the hydraulic conductivity of a porous material, comprising:
    means for enclosing a partially saturated sample of a porous material;
    means for mounting the enclosing means for rotation about an axis thereof;
    means carried by the mounting means for establishing a dynamic equilibrium of the enclosing means; and,
    means for measuring the rate of rotation of the enclosing means under dynamic equilibrium, the rate of rotation being directly related to the hydraulic conductivity of the sample.

2. The apparatus of claim 1 wherein the enclosing means comprise:
    a. at least two concentric cylinders of substantially equal length defining at least one annular chamber therebetween; and
    b. means for sealing said at least one annular chamber.

3. The apparatus of claim 1 and further comprising port means formed in the enclosing means for communicating with the interior thereof to move fluid material therethrough.

4. The apparatus of claim 1 wherein the second-mentioned means comprises a rod mounted for rotary movement and the third-mentioned means comprises a mass mounted to the rod to apply torque to the enclosing means.

5. A method for measuring a quantity directly related to the hydraulic conductivity of a porous material, comprising:
    enclosing a dry sample of the porous material within a substantially annular chamber mounted for free rotation about an axis;
    balancing the chamber enclosing the sample;
    adjusting the level of saturation of the sample to a desired value;
    applying a torque to the chamber to effect rotation, allowing the establishment of a dynamic equilibrium whereby the rotation of the chamber becomes constant; and,
    measuring the rate of rotation of the chamber, said rate of rotation being directly related to the hydraulic conductivity of the sample.

6. The method of claim 5 wherein the sample is dry when initially placed within the chamber, the method further comprising after balancing of the chamber the step of disposing a saturating fluid within the chamber to saturate the sample.

7. The apparatus of claim 2 wherein said at least two concentric cylinders include first and second right circular cylinders.

8. The apparatus of claim 1 wherein said dynamic equilibrium establishing means includes means for rotating said enclosing means at a substantially constant rate.

9. The apparatus of claim 8 wherein said constant rate rotating means includes a mass mounted to said mounting means for applying a torque to said enclosing means.

10. The apparatus of claim 9 wherein said mounting means includes a rod mounted for rotary movement, said mass being mounted to said rod.

11. Apparatus for measuring a quantity directly related to hydraulic conductivity of a porous material, comprising
    a. at least two concentric cylinders of substantially equal length defining at least one annular chamber therebetween;
    b. means for sealing said at least one annular chamber, at least a portion of said at least one annular chamber containing a partially saturated sample of a porous material;
    c. means for mounting said at least two concentric cylinders for rotation about an axis thereof;

d. means carried by the mounting means for establishing a dynamic equilibrium of said at least two concentric cylinders; and e. means for measuring the rate of rotation of said at least two concentric cylinders under dynamic equilibrium, the rate of rotation being directly related to the hydraulic conductivity of said sample.

12. The apparatus of claim 11 wherein said at least two concentric cylinders includes first and second right circular cylinders.

13. The apparatus of claim 11 further comprising port means for communicating with said annular chamber to move fluid material thereinto.

14. The apparatus of claim 11 wherein said dynamic equilibrium establishing means includes a mass mounted to said mounting means for applying a torque to said at least two concentric cylinders.

15. The apparatus of claim 14 wherein said mounting means includes a rod mounted for rotary movement, said mass being mounted to said rod.

16. Apparatus for measuring a quantity directly related to the hydraulic conductivity of a porous material, comprising:

a. means for enclosing a partially saturated sample of a porous material;

b. means for mounting said enclosing means for rotation about an axis thereof;

c. means carried by said mounting means for establishing a substantially constant rate of rotation of said enclosing means thereby establishing a dynamic equilibrium for said enclosing means;

d. means for measuring the rate of rotation of said enclosing means under dynamic equilibrium, the rate of rotation being directly related to the hydraulic conductivity of the sample.

17. The apparatus of claim 16 wherein said rotation establishing means includes a mass mounted to said mounting means for applying a torque to said enclosing means.

18. The apparatus of claim 17 wherein said mounting means includes a rod mounted for rotary movement, said mass being mounted to said rod.

19. The apparatus of claim 17 wherein said enclosing means includes:

a. at least two concentric cylinders of substantially equal length defining at least one annular chamber therebetween; and b. means for sealing said at least one annular chamber.

20. The apparatus of claim 19 wherein said at least two concentric cylinders include first and second right circular cylinders.

* * * * *